United States Patent
King et al.

(10) Patent No.: US 12,303,654 B2
(45) Date of Patent: May 20, 2025

(54) ENDOSCOPIC APPLICATOR WITH REAGENT BALL CUTTER

(71) Applicant: Boston Scientific Scimed, Inc., Maple Grove, MN (US)

(72) Inventors: Joseph W. King, Franklin, MA (US); Gonzalo Jose Saenz Villalobos, Alajuela (CR); John T. Favreau, Charlton, MA (US); Lauren S. Lydecker, Millbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/396,021

(22) Filed: Dec. 26, 2023

(65) Prior Publication Data

US 2024/0123190 A1    Apr. 18, 2024

Related U.S. Application Data

(63) Continuation of application No. 18/067,324, filed on Dec. 16, 2022, now Pat. No. 11,890,430, which is a
(Continued)

(51) Int. Cl.
*A61M 25/01* (2006.01)
*A61M 25/00* (2006.01)
*A61M 25/02* (2006.01)

(52) U.S. Cl.
CPC .... *A61M 25/0113* (2013.01); *A61M 25/0074* (2013.01); *A61M 25/0136* (2013.01); *A61M 2025/0266* (2013.01)

(58) Field of Classification Search
CPC ............ A61M 37/0069; A61M 35/003; A61M 25/0113; A61M 25/0074; A61M 25/0136;
(Continued)

(56) References Cited

U.S. PATENT DOCUMENTS 3,238,941 A * 3/1966 Klein .................... A61M 31/00
604/218
4,302,481 A    11/1981 Ribnitz et al.
(Continued)

FOREIGN PATENT DOCUMENTS

CN    103648355 A    3/2014
CN    103958629 A    7/2014
(Continued)

OTHER PUBLICATIONS

Machine translation of KR-20160046435-A into English.
(Continued)

*Primary Examiner* — Nathan R Price
*Assistant Examiner* — Adam J. Cermak
(74) *Attorney, Agent, or Firm* — Bookoff McAndrews PLLC

(57) ABSTRACT

A medical dispensing device which includes a catheter, an applicator tip at a distal end of the catheter, the catheter and the applicator tip defining a lumen having a longitudinal axis and a distal opening, a plunger in the lumen and movable along the longitudinal axis, and a plurality of elements in the lumen proximal to the distal opening and distal to the plunger, the plurality of elements stacked along the longitudinal axis for dispersement of one element at a time through the distal opening via a force applied by the plunger.

18 Claims, 7 Drawing Sheets

Related U.S. Application Data continuation of application No. 16/860,252, filed on Apr. 28, 2020, now Pat. No. 11,554,251.

(60) Provisional application No. 62/840,734, filed on Apr. 30, 2019.

(58) Field of Classification Search
CPC ...... A61M 2025/0266; A61M 39/0067; A61M 39/007; A61M 2202/06; A61M 25/0068; A61M 25/008; A61B 17/00592; A61B 17/00491; A61B 2017/0065; A61B 2017/00592; A61B 2017/00495; A61B 2017/00491; A61B 17/12022; A61B 17/12027; A61B 17/1204; A61B 17/12031; A61B 17/12036; A61B 17/12131; A61B 17/12159; A61B 17/12163; A61B 17/12168; A61B 17/12172; A61F 13/00085; A61F 15/005
See application file for complete search history.

(56) References Cited

U.S. PATENT DOCUMENTS

| | | | | |
|---|---|---|---|---|
| 4,700,692 A * | 10/1987 | Baumgartner | .... | A61M 37/0069 600/7 |
| 5,147,374 A | 9/1992 | Fernandez | | |
| 5,251,641 A * | 10/1993 | Xavier | ............ | A61B 10/0266 600/567 |
| 5,281,197 A * | 1/1994 | Arias | ............ | A61M 37/0069 604/209 |
| 5,366,113 A * | 11/1994 | Kim | ............ | A61J 7/0053 206/537 |
| 5,415,631 A | 5/1995 | Churinetz et al. | | |
| 5,425,757 A * | 6/1995 | Tiefenbrun | ...... | A61B 17/12109 128/898 |
| 5,464,404 A * | 11/1995 | Abela | ............ | A61B 18/24 606/41 |
| 5,681,279 A * | 10/1997 | Roper | ............ | A61J 7/0053 606/236 |
| 5,824,082 A | 10/1998 | Brown | | |
| 5,873,886 A * | 2/1999 | Larsen | ............ | A61B 17/32002 606/167 |
| 6,050,986 A | 4/2000 | Hektner | | |
| 6,197,324 B1* | 3/2001 | Crittenden | ............ | A61K 31/00 424/423 |
| 6,238,416 B1* | 5/2001 | Sideris | ............ | A61B 17/0057 128/897 |
| 6,251,418 B1* | 6/2001 | Ahern | ............ | A61M 37/0069 424/423 |
| 6,347,241 B2* | 2/2002 | Burbank | ............ | A61M 37/0069 600/431 |
| 6,450,937 B1* | 9/2002 | Mercereau | ............ | A61N 5/1007 600/7 |
| 6,530,934 B1* | 3/2003 | Jacobsen | ............ | A61B 17/12113 606/157 |
| 6,547,769 B2 | 4/2003 | VanTassel et al. | | |
| 6,602,218 B2* | 8/2003 | Yoon | ............ | A61B 17/0218 606/49 |
| 6,802,822 B1* | 10/2004 | Dodge | ............ | A61B 17/00491 604/82 |
| 7,232,421 B1* | 6/2007 | Gambale | ............ | A61M 37/0069 604/57 |
| 7,306,390 B2* | 12/2007 | Quintero | ............ | B05C 17/0116 401/133 |
| 7,699,191 B2* | 4/2010 | Sheets, Jr. | ......... | A61B 17/00491 604/311 |
| 7,780,700 B2* | 8/2010 | Frazier | ............ | A61B 17/12122 606/151 |
| 7,946,453 B2* | 5/2011 | Voegele | ............ | A61B 17/00491 222/134 |
| RE42,959 E * | 11/2011 | Saadat | ............ | A61M 37/0069 606/7 |
| 8,357,169 B2* | 1/2013 | Henniges | ............ | A61B 17/8816 606/92 |
| 8,584,973 B2 | 11/2013 | Mather et al. | | |
| 8,961,479 B2* | 2/2015 | Hen | ............ | A61B 17/12163 604/290 |
| 8,968,235 B2* | 3/2015 | Solomon | ............ | A61M 37/0069 604/60 |
| 9,039,761 B2* | 5/2015 | Trogden | ............ | A61F 9/0017 623/6.12 |
| 9,622,778 B2* | 4/2017 | Wengreen | ............ | A61M 37/0069 |
| 9,999,758 B2* | 6/2018 | Vetter | ............ | A61B 17/3468 |
| 11,890,430 B2* | 2/2024 | King | ............ | A61M 25/0113 |
| 2003/0208153 A1* | 11/2003 | Stenzel | ............ | A61B 17/3417 604/60 |
| 2004/0064136 A1 | 4/2004 | Papineau et al. | | |
| 2004/0186423 A1 | 9/2004 | Cafferata | | |
| 2004/0190975 A1* | 9/2004 | Goodman | ............ | B05C 17/002 401/134 |
| 2005/0013957 A1 | 1/2005 | Leschinsky | | |
| 2006/0058867 A1 | 3/2006 | Thistle et al. | | |
| 2007/0125483 A1 | 6/2007 | Barnett et al. | | |
| 2007/0219612 A1* | 9/2007 | Andreas | ............ | A61B 17/12022 623/1.11 |
| 2008/0109057 A1* | 5/2008 | Calabria | ............ | A61L 31/14 623/1.11 |
| 2008/0112751 A1* | 5/2008 | Sheets | ............ | A61B 17/00491 401/134 |
| 2008/0114315 A1* | 5/2008 | Voegele | ............ | A61B 17/00491 604/311 |
| 2009/0283547 A1* | 11/2009 | Harrold | ............ | B05B 11/1092 222/256 |
| 2010/0331868 A1* | 12/2010 | Bardy | ............ | A61M 37/0069 606/167 |
| 2011/0060407 A1* | 3/2011 | Ketai | ............ | A61B 17/0644 623/2.37 |
| 2012/0101482 A1 | 4/2012 | Flores et al. | | |
| 2012/0259349 A1* | 10/2012 | Brahm | ............ | A61B 17/00 606/151 |
| 2013/0006101 A1* | 1/2013 | McHugo | ............ | A61B 90/39 600/432 |
| 2013/0035704 A1* | 2/2013 | Dudai | ............ | A61F 2/0063 606/151 |
| 2013/0046331 A1* | 2/2013 | Christensen | ........ | A61B 17/1214 606/200 |
| 2013/0079811 A1* | 3/2013 | Agnew | ............ | A61B 17/0057 606/213 |
| 2013/0110080 A1* | 5/2013 | Ducharme | ............ | A61M 5/155 604/506 |
| 2013/0261660 A1* | 10/2013 | McKay | ............ | A61F 13/15252 606/213 |
| 2014/0012094 A1 | 1/2014 | Das et al. | | |
| 2014/0148839 A1* | 5/2014 | Pavcnik | ............ | A61B 17/0057 606/191 |
| 2014/0213932 A1* | 7/2014 | Knoll | ............ | A61B 10/0233 600/567 |
| 2014/0371586 A1* | 12/2014 | Ryan | ............ | A61M 37/0069 600/431 |
| 2015/0173772 A1* | 6/2015 | Bowman | ............ | A61M 25/09041 606/200 |
| 2016/0120551 A1* | 5/2016 | Connor | ............ | A61F 2/91 606/200 |
| 2016/0166257 A1* | 6/2016 | Allen | ............ | A61B 17/12109 606/200 |
| 2016/0262761 A1* | 9/2016 | Beisel | ............ | A61B 17/1114 |
| 2017/0014569 A1* | 1/2017 | Flanagan | ............ | A61M 5/155 |
| 2017/0035417 A1* | 2/2017 | Cohn | ............ | A61B 17/10 |
| 2017/0224357 A1* | 8/2017 | Whalen | ............ | A61B 17/135 |
| 2017/0319214 A1* | 11/2017 | Rudakov | ............ | A61B 17/12172 |
| 2018/0019357 A1 | 1/2018 | Wheelwright et al. | | |
| 2018/0256139 A1* | 9/2018 | Miller | ............ | A61F 6/22 |
| 2018/0368857 A1* | 12/2018 | Willard | ............ | A61B 17/12031 |
| 2019/0070342 A1* | 3/2019 | Hakimimehr | ........ | A61K 9/0075 |
| 2019/0374228 A1* | 12/2019 | Wallace | ............ | A61B 17/1214 |

(56) References Cited

U.S. PATENT DOCUMENTS

2021/0162175 A1    6/2021  Favreau et al.
2022/0226018 A1*   7/2022  Virden .............. A61M 37/0069

FOREIGN PATENT DOCUMENTS

| EP | 1096919 B1 | 2/2005 |
|---|---|---|
| EP | 3007640 B1 | 1/2020 |
| EP | 3178410 B1 | 3/2020 |
| JP | 2020039895 A | 3/2020 |
| KR | 20070093884 A | 9/2007 |
| KR | 20120010837 A | 2/2012 |
| KR | 20160046435 A | 4/2016 |
| WO | 2001093920 A2 | 12/2001 |
| WO | 2005030315 A1 | 4/2005 |
| WO | 2009064839 A1 | 5/2009 |
| WO | 2011034973 A2 | 3/2011 |
| WO | 2013055568 A1 | 4/2013 |
| WO | 2017011668 A1 | 1/2017 |

OTHER PUBLICATIONS

Office Action in Chinese Application No. 202080030255.6, dated Nov. 21, 2023 (8 pages).
Office Action in Japanese Application No. 2021-564255, dated Jan. 9, 2024 (6 pages).

* cited by examiner

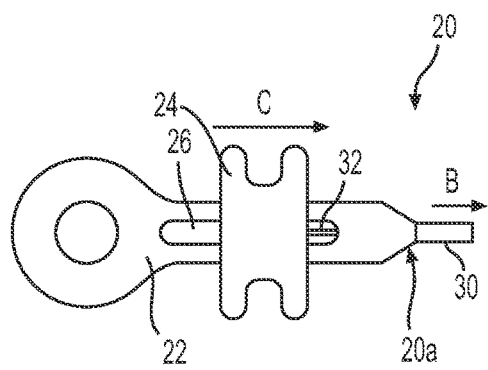
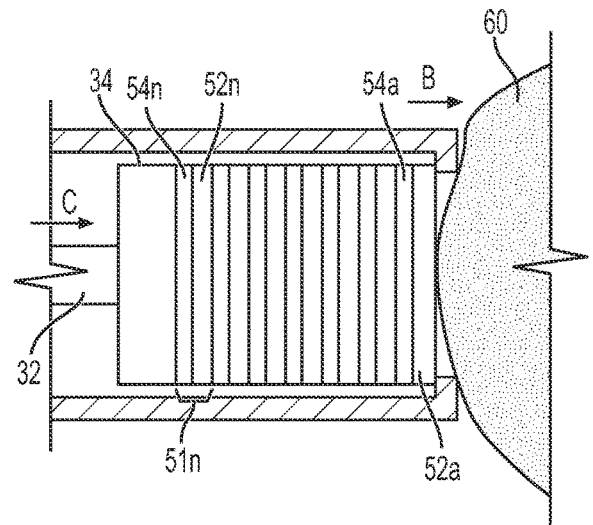
FIG. 4A  FIG. 4B
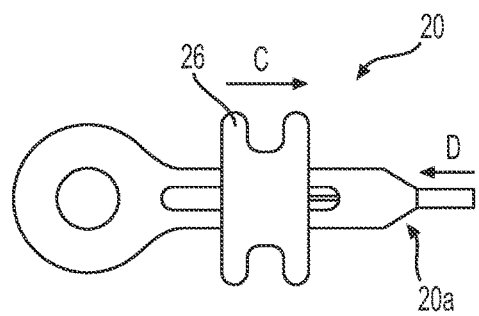
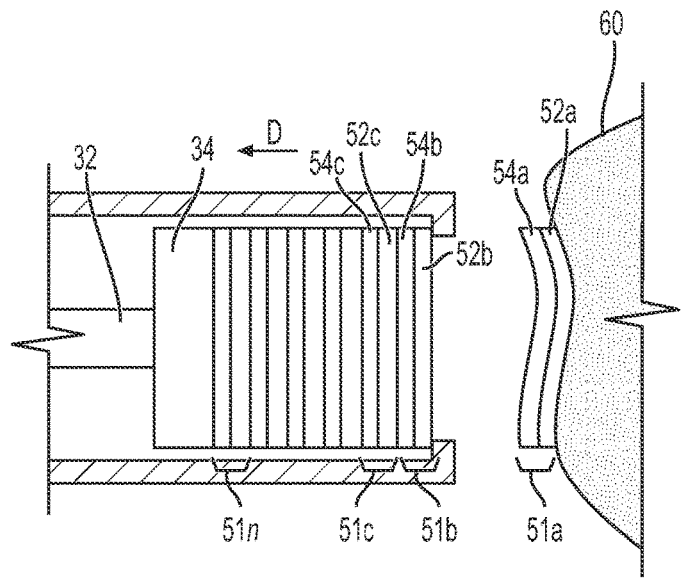
FIG. 5A  FIG. 5B

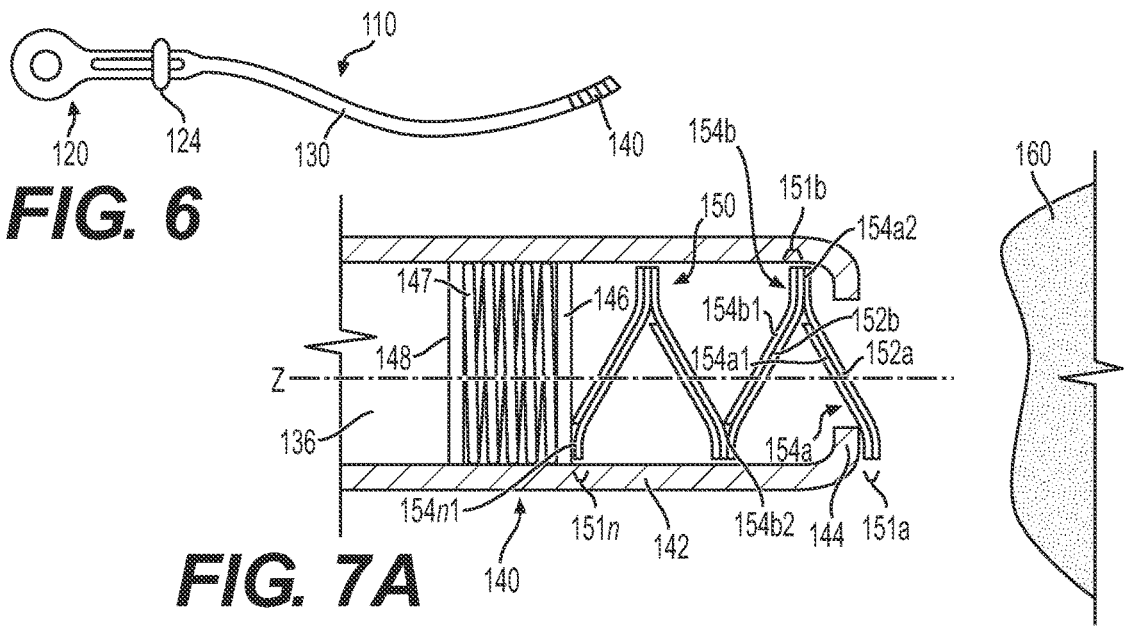
FIG. 6
FIG. 7A
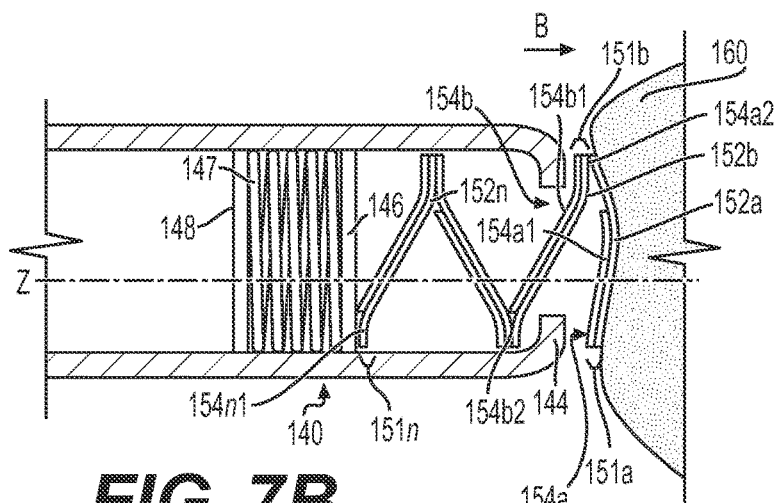
FIG. 7B
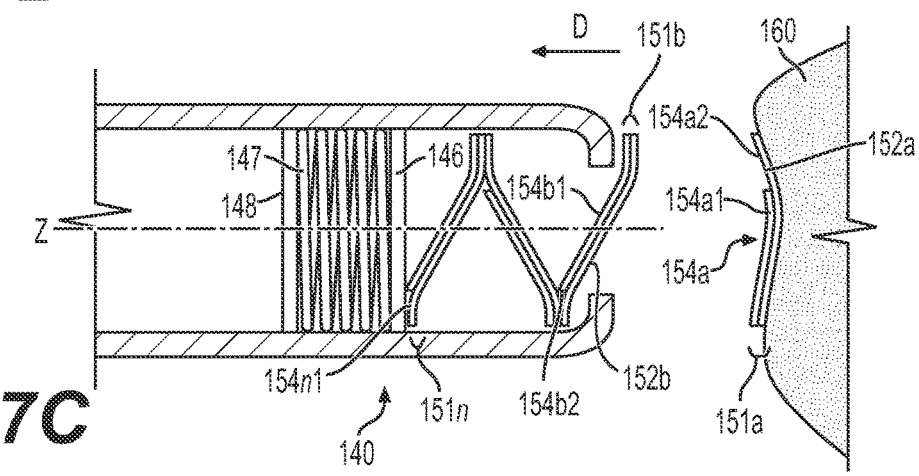
FIG. 7C

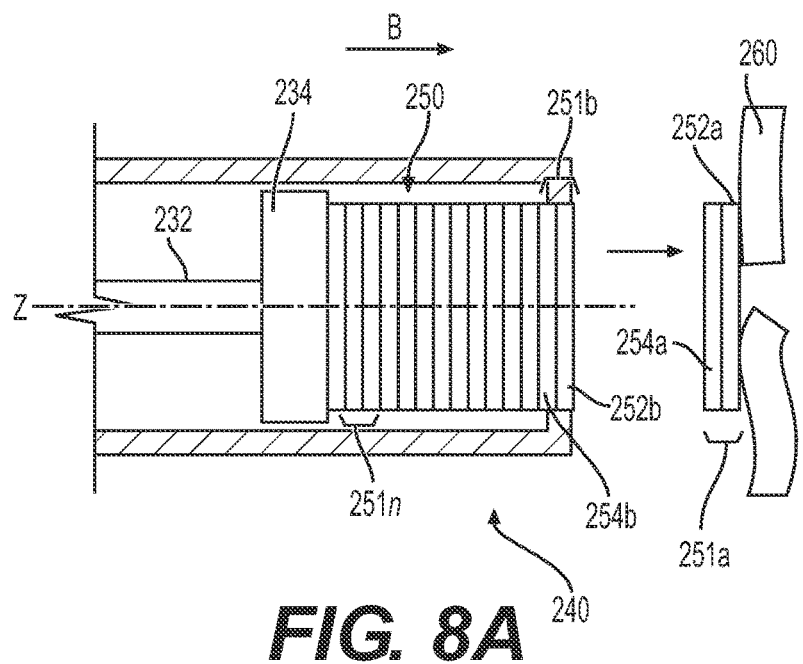
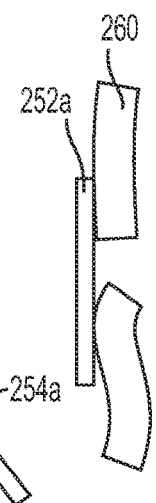
FIG. 8A    FIG. 8B
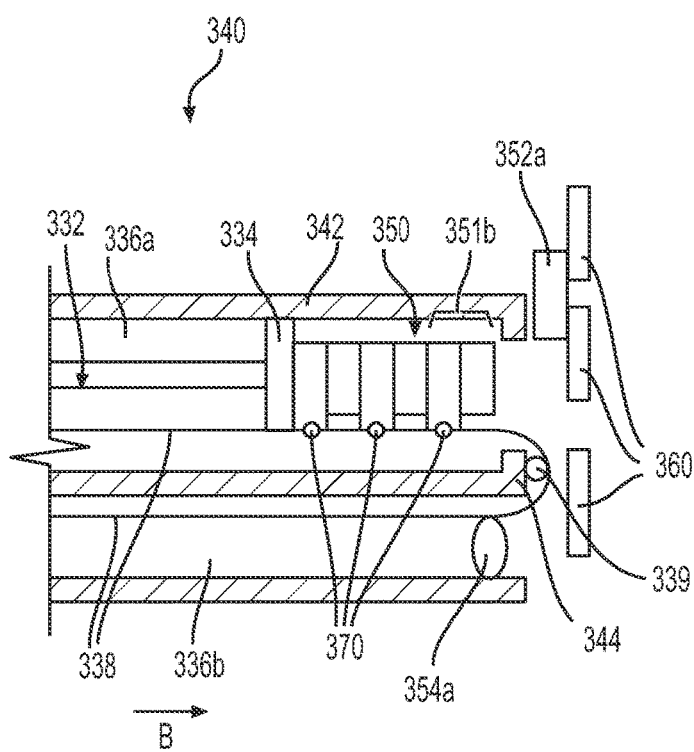
FIG. 9

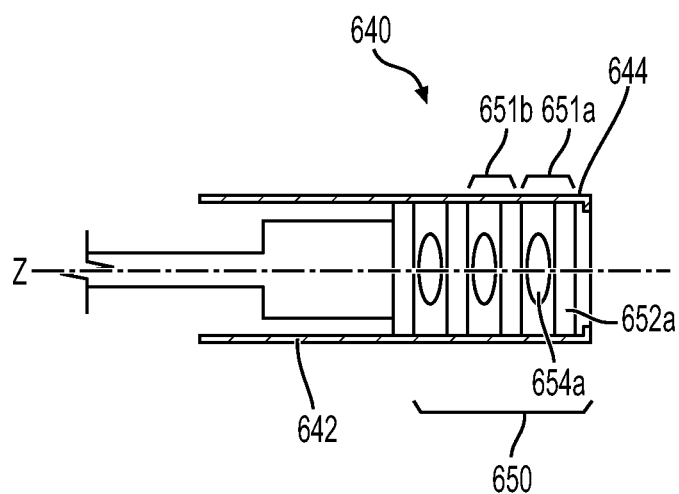
FIG. 12A
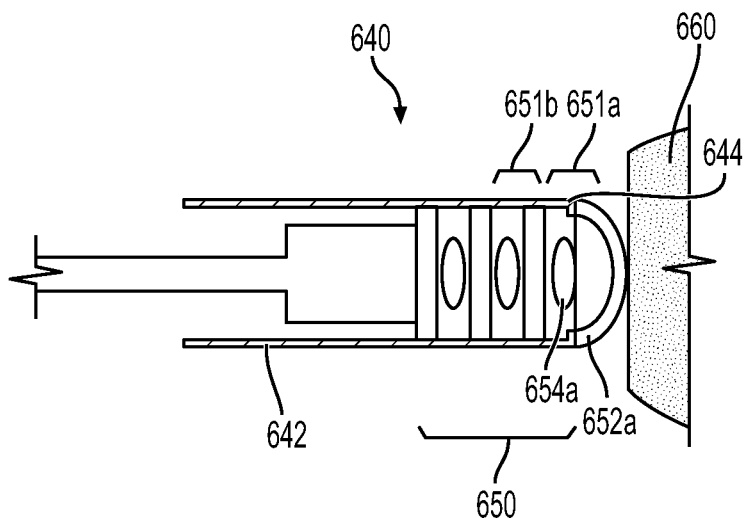 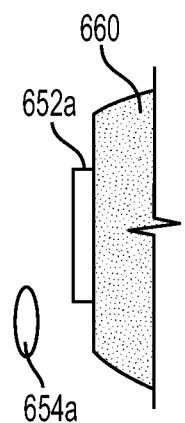
FIG. 12B

ENDOSCOPIC APPLICATOR WITH REAGENT BALL CUTTER

CROSS-REFERENCE TO RELATED APPLICATIONS

This application is a continuation of U.S. application Ser. No. 18/067,324, filed Dec. 16, 2022, now U.S. Pat. No. 11,890,430, which is a continuation of U.S. application Ser. No. 16/860,252, filed Apr. 28, 2020, now U.S. Pat. No. 11,554,251, which claims the benefit of priority from U.S. Provisional Application No. 62/840,734, filed Apr. 30, 2019, each of which is incorporated by reference herein in its entirety.

TECHNICAL FIELD

The present disclosure relates generally to medical systems and devices for delivering protective barriers to the gastrointestinal (GI) region, and more particularly, to methods and tools for delivering and deploying patches or other tissue barriers to the gastrointestinal system.

BACKGROUND

Conventional endoscopic procedures, such as endomucosal resection (EMR), endosubmucosal dissection (ESD), and anastomosis, as well as diseases, such as inflammatory bowel disease (IBD) and IBD subsidiary diseases, result in damage to GI tissues. These procedures and diseases cause very thin layers in the GI tract wall, leaving the GI tract wall vulnerable to GI perforation or other trauma.

Current procedures for repairing the GI tract require surgical procedures, including clipping or endoscopic suturing, to appose tissue and allow time for healing. These conventional techniques and associated technologies are not suitable for large defects, or for repair of friable or fibrotic tissue. Yet, failure to provide a protective barrier between the damaged GI tract lining and the GI cavity can cause perforation, infection, and/or sepsis. The present disclosure may solve one or more of these problems or other problems in the art. The scope of the disclosure, however, is defined by the attached claims and not the ability to solve a specific problem.

SUMMARY OF THE DISCLOSURE

According to an embodiment, a medical dispensing device comprises a catheter defining a lumen having a longitudinal axis and a distal opening, a plunger disposed in the lumen and movable along the longitudinal axis, and a plurality of elements disposed in the lumen proximal to the distal opening and distal to the plunger, the plurality of elements being stacked along the longitudinal axis for dispersement one element at a time through the distal opening via a force applied by the plunger.

The device may include a wire or a cable disposed in the lumen and connected to a proximal end of the plunger, and the wire or the cable may be configured to move the plunger axially along the longitudinal axis.

The plurality of elements may include a plurality of stacked patches, and each of the plurality of stacked patches may have an adhesive layer and a non-adhesive layer proximal to the adhesive layer.

The non-adhesive layer may be configured to remain attached to the adhesive layer after dispensing the respective patch from the device.

The non-adhesive layer may not extend across an entire proximal surface of the adhesive layer, exposing a portion of the proximal surface of the adhesive layer, and the exposed portion of the proximal surface may be attached to (1) a distal surface of the adhesive layer of an adjacent and proximal patch from the plurality of stacked patches, or (2) the plunger.

A proximal surface of the non-adhesive layer of a distalmost patch of the plurality of stacked patches may be configured to contact a distalmost surface of the catheter outside of the lumen.

The device may include a second wire or a second cable extending from a proximal end to a distal end of the catheter and may be attached to each of the non-adhesive layers, and may be configured to remove each separate non-adhesive layer from a corresponding adhesive layer.

The device may include a second lumen defined by the catheter, the second wire or the second cable may extend through the second lumen, and the second lumen may receive each of the non-adhesive layers separate from the corresponding adhesive layer.

Each of the adhesive layers may include one or more therapeutic agents.

The distal end of the catheter may include an annular ring at a distalmost portion of the catheter and extending from a sidewall of the catheter toward the distal opening, wherein a distance between an innermost surface of the annular ring and the longitudinal axis may be less than a distance between an innermost surface of the sidewall of the catheter and the longitudinal axis.

A distal surface of a distalmost element of the plurality of elements may be configured to contact a proximal surface of the annular ring, and the force applied by the plunger may push the distalmost element out the distal opening.

The device may include a wall disposed in the lumen, transverse to the longitudinal axis, and fixed to a sidewall of the lumen at a location proximal to the plurality of elements, and may include a biasing element attached at a first end to the wall, and at a second end to the plunger, such that a force provided by the biasing element may push the plunger against the plurality of elements and toward the distal opening.

The plurality of elements may include a plurality of deformable spheres, an outer surface of each of the deformable spheres including a first material and surrounding and containing therein a second material, different from the first material.

A protrusion may extend from a sidewall defining the lumen toward the longitudinal axis, and distal to a distalmost one of the plurality of deformable spheres.

The device may include one or more cutters distal to the protrusion and extending from the sidewall defining the lumen toward the longitudinal axis, wherein the one or more cutters may be configured to cut the outer surface of each of the plurality of deformable spheres and expose the second material as each of the plurality of deformable spheres is dispensed from the device.

According to another embodiment, a medical dispensing device includes a handle, a catheter extending distally from the handle, an applicator tip at a distal end of the catheter, the catheter and the applicator tip defining a lumen having a longitudinal axis and a distal opening, a plunger disposed in the lumen and movable along the longitudinal axis, and a plurality of elements disposed in the lumen proximal to the distal opening and distal to the plunger, the plurality of elements being stacked along the longitudinal axis for dispersement one element at a time through the distal opening.

The plurality of elements may include a plurality of deformable spheres, an outer surface of each of the deformable spheres including a first material and surrounding and containing therein a second, flowable material, different from the first material.

The plurality of elements may include a plurality of stacked patches, each of the plurality of stacked patches may have an adhesive layer and a non-adhesive layer proximal to the adhesive layer.

According to yet another embodiment, a method for applying a medical patch to tissue includes pushing a stack of patches toward a distal opening of a catheter, moving the catheter toward a target, such that a distalmost patch from the stack of patches contacts the target, and moving the catheter in a proximal direction, away from the target, thereby releasing the distalmost patch from the catheter.

The method may include, after releasing the distalmost patch from the catheter, pushing the remaining patches of the stack of patches toward the distal opening, moving the catheter toward a second target, such that a second distalmost patch contacts the second target, and moving the catheter in a proximal direction, away from the second target, thereby releasing the second distalmost patch from the catheter

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 4A is a perspective view of a handle for an endoscopic applicator system according to an embodiment;

FIG. 4B is a cross-section of an applicator tip according to an embodiment;

FIG. 5A is a perspective view of a handle for an endoscopic applicator system according to an embodiment;

FIG. 5B is a cross-section of an applicator tip according to an embodiment;

FIG. 6 is a schematic of an endoscopic applicator system according to another embodiment;

FIGS. 7A-7C are cross-sections of an applicator tip according to another embodiment;

FIG. 8A is a cross-section of an applicator tip according to yet another embodiment;

FIG. 8B is a cross-section of a regenerative patch according to an embodiment;

FIG. 9 is a cross-section of an applicator tip according to yet another embodiment;

FIGS. 12A-12B are cross-sections of an applicator tip according to yet another embodiment.

DETAILED DESCRIPTION

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Figure 1:
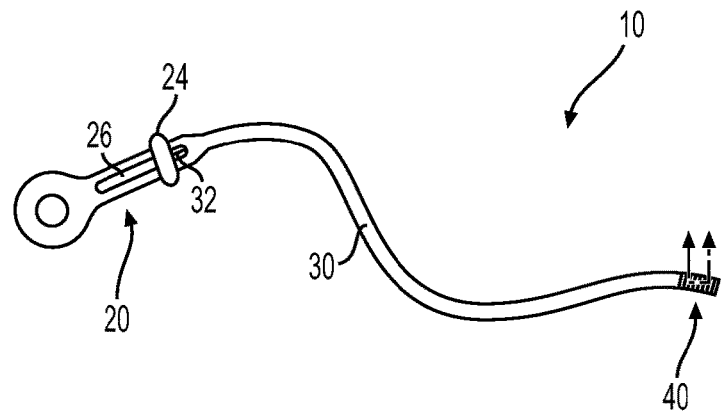
FIG. 1 is a schematic of an endoscopic applicator system according to an embodiment.

Referring to FIG. 1, an endoscopic applicator 10 according to an embodiment is shown. Endoscopic applicator 10 includes a handle 20, a catheter 30 connected to handle 20, and an applicator tip 40 at a distal end of catheter 30, opposite handle 20.

Figure 2:
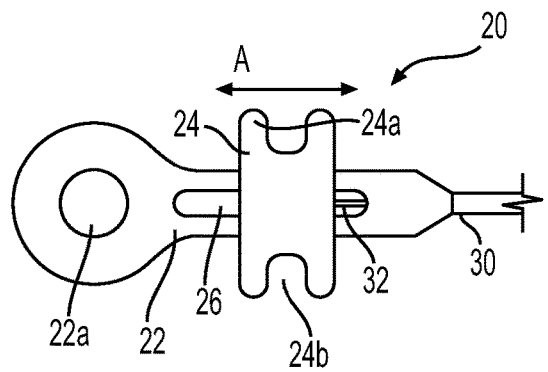
FIG. 2 is a perspective view of a handle for an endoscopic applicator system according to an embodiment.

FIG. 2 illustrates handle 20 according to an exemplary embodiment. Handle 20 includes a body 22 defining a hole 22a in body 22 at a proximal end thereof. Catheter 30 is attached at an opposite, distal end of body 22. A slot 26 extends through body 22 in a direction parallel to a direction of extension of catheter 30. A spool 24 is disposed in slot 26 and moves within and along slot 26 in a direction parallel to the direction of extension, as shown by arrow A. As further shown in FIG. 2, spool 24 includes two annular protrusions 24a at a distal end and a proximal end thereof and extending from spool 24 in a direction perpendicular to the direction of extension of catheter 30. Annular protrusions 24a define an annular grip 24b, which is grasped by a user as will be described in greater detail herein. It will be understood that handle 20 may be made of any material known in the art, including, but not limited to, a medical grade plastic or rubber, a ceramic, a metal, or a combination thereof.

As further shown in FIG. 2, a wire 32 (or a cable) extends distally from the distal end of spool 24. Wire 32 extends through a hole (not shown) in handle 20 and into a lumen 36 (FIG. 3) of catheter 30. As will be described in greater detail herein, actuation of wire 32 dispenses a regenerative patch. As will be understood, catheter 30 is a generally circular sheath extending from handle 20 to applicator tip 40. While catheter 30 is described as including lumen 36 (FIG. 3), catheter 30 may include multiple lumens to incorporate other tools and/or elements (e.g., lighting, imaging, etc.) at applicator tip 40. Additionally, or alternatively, catheter 30 may be placed in another, larger catheter or endoscope (not shown), if use of tools, suction, light-emitting elements, or the like associated with the larger catheter are so desired. It will be understood that wire 32 may include any material known in the art, including, but not limited to, medical grade plastic, metal, or other resin suitable to be used to push and/or pull a plunger 34 (FIG. 3), as described herein, during application of a regenerative patch or agent. It will be understood that while examples discuss a regenerative agent applied to a patch, the patch may include an adhesive without a regenerative agent. Further, it will be understood that catheter 30 may be formed of any medical grade plastic, rubber, resin, or the like that is suitable for use in medical applications.

Figure 3:
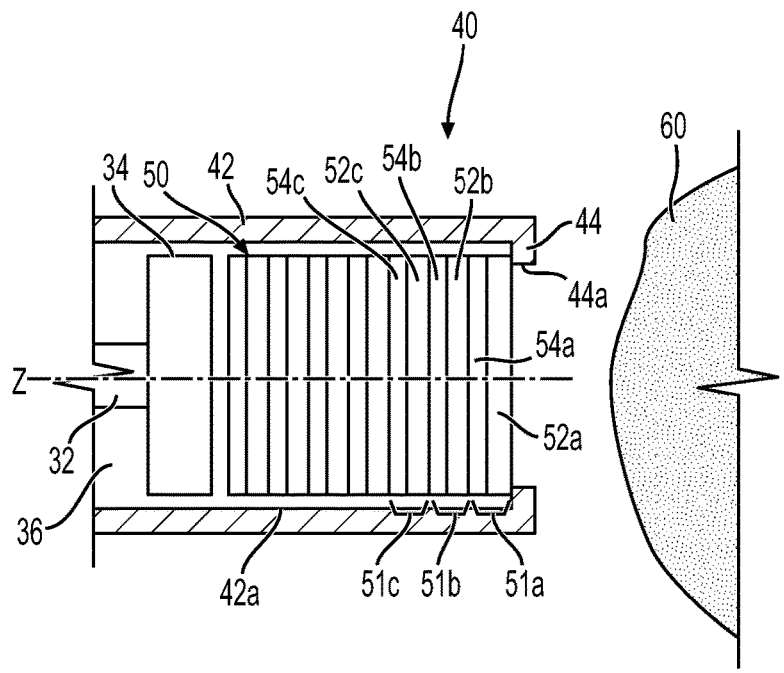
FIG. 3 is a cross-section of an applicator tip according to an embodiment.

Referring to FIG. 3, which shows a cross-section of applicator tip 40, as indicated by the cross-sectional lines shown in FIG. 1, applicator tip 40 is disposed at the distal end of catheter 30. Applicator tip 40 includes an outer wall 42 having a generally circular cross-section. As shown in FIG. 3, applicator tip 40 is the distalmost portion of catheter 30, as applicator tip 40 may be integrally formed with catheter 30. Applicator tip 40 further includes an annular ring 44 provided at a distalmost portion of applicator tip 40.

Annular ring 44 extends annularly from an outermost part of outer wall 42 toward a central longitudinal axis Z (e.g., central axis Z) of lumen 36, has a uniform thickness, and forms a radially-inward directed flange at the distalmost end of endoscopic applicator 10. The flange assists in retaining patches within applicator tip 40. A distance from central axis Z to an innermost portion 44a of annular ring 44 is less than a distance from central axis Z to an innermost portion 42a of outer wall 42. Alternatively, or additionally, applicator tip 40, including outer wall 42, may be a separate element from catheter 30, such as an add on device attached via screw threads, adhesive, snap fit, or the like. Applicator tip 40 may be any material known in the art, including, but not limited to, a medical grade plastic, resin, or rubber. Alternatively, any other mechanism for retaining patches 50, e.g., tabs, may be provided at the distalmost portion of applicator tip 40.

As shown in FIG. 3, a stack of patches 50, for example patches having a regenerative agent, are disposed in applicator tip 40 for application to a target 60, as explained herein. Plunger 34, connected to a distalmost portion of wire 32, is disposed in applicator tip 40 at a position proximal to the stack of patches 50. Plunger 34 may be any material known in the art, including, but not limited to a medical grade metal alloy, a plastic, a resin, or a rubber, suitable for being used to place pressure against the stack of patches 50.

With continued reference to FIG. 3, the stack of patches 50 may include a first patch 51a having a first layer 52a including an adhesive substance and a second layer 54a including a non-adhesive backing, so that adjacent patches 50 do not adhere to one another. As described herein, first layer 52a may include a regenerative agent, an adhesive regenerative agent, or any other therapeutic or diagnostic agent and/or attachment mechanism for attaching first patch 51a to target 60.

First layer 52a is provided at a distalmost position of lumen 36 and is adjacent to and in contact with annular ring 44 of applicator tip 40. First layer 52a is applied to target 60, e.g., tissue, or another suitable target site, as will be described herein. A second patch 51b having a first layer 52b including an adhesive agent (and/or a regenerative agent) and a second layer 54b including a non-adhesive backing is disposed proximal to and adjacent second layer 54a of first patch 51a. A third patch 51c having a first layer 52c and a second layer 54c is disposed proximal to and adjacent second layer 54b of second patch 51b, and so on and so forth for n number of patches (an n patch 51n is illustrated in FIG. 4B and has a first layer 52n and a second layer 54n). It will be understood that target 60 may be any tissue known in the art, including but not limited to endomucosal tissue, gastrointestinal tissue, bone tissue, cartilage, etc.

An operation of endoscopic applicator 10 illustrated in FIGS. 1-3 will now be described.

Endoscopic applicator 10 is introduced to the body through an opening, such as through the mouth or nose, or through an opening formed by an incision, e.g., during a surgical procedure. Applicator tip 40 is inserted into the body through the opening and advanced to the desired deployment site, e.g., the GI tract. According to an embodiment, applicator tip 40 and catheter 30 are advanced along a guidewire (not shown). It will be understood that applicator tip 40 and catheter 30 may be advanced along a pre-positioned sheath, catheter, endoscope, bronchoscope, colonoscope, or the like, e.g., a catheter with multiple lumens to provide light emission, suction, tools, or the like, or may be positioned in any other manner or using any other device known in the art.

After positioning applicator tip 40 at the desired location, e.g., at target 60, deployment and placement of the stack of patches 50, one-by-one in a serial fashion, is performed. Referring to FIGS. 4A and 4B, handle 20 is maneuvered to push the distalmost portion of applicator tip 40, including annular ring 44, in a direction indicated by arrows B, such that annular ring 44 abuts target 60. At a same time, or subsequently, spool 24 (grasped by an index finger and a middle finger of the user's hand, while a thumb is in hole 22a, for example) is advanced longitudinally along handle 20 in a direction indicated by arrow C toward a distal end 20a of handle 20, thereby pushing wire 32 and plunger 34 in the direction indicated by arrow C in FIG. 4B. Plunger 34 pushes against the proximalmost patch 51n (n is a number of patches in the stack of patches 50, and may be a maximum number of patches in the stack of patches 50 that can be disposed in applicator tip 40), thereby forcing the stack of patches 50 against target 60, and causing first layer 52a of first patch 51a to contact and adhere to target 60. Subsequently, while continuing to push spool 24 toward distal end 20a of handle 20, or maintaining a position of spool 24 relative to handle 20, endoscopic applicator 10, including applicator tip 40, is pulled in a proximal direction, as indicated by arrow D in FIGS. 5A and 5B. As shown in FIG. 5B, first patch 51a adheres to target 60 via first layer 52a, and second layer 54a remains attached to a side of first layer 52a opposite target 60. After application of first patch 51a, applicator tip 40 is moved to another application location, e.g., a position adjacent first patch 51a, and the application of second patch 52a is performed. In this manner, one or more patches from the stack of patches 50 is applied to target 60.

Referring to FIG. 6, an endoscope applicator 110 according to another embodiment is disclosed. Like reference numerals will be used to describe like elements.

Endoscope applicator 110 includes a handle 120, a catheter 130 attached to handle 120, and an applicator tip 140 attached to catheter 130 at a distal end opposite handle 120. Spool 124 is shown in FIG. 6; however, since a spool is unnecessary in the operation of endoscope applicator 110 according to the embodiment in FIGS. 6-7C as described herein, handle 120 may be formed without spool 124. With continued reference to FIG. 6, catheter 130 is a generally circular sheath extending from handle 120 to applicator tip 140 and defining a lumen 136, similar to catheter 30 described above.

Referring to FIG. 7A, applicator tip 140 according to an embodiment will be described. Applicator tip 140 is disposed at a distal end of catheter 130. Applicator tip 140 includes an outer wall 142 and an annular ring 144, similar to applicator tip 40. As shown in FIG. 7A, a stack of patches 150 is disposed in applicator tip 140 for application to a target 160, as explained herein. A plunger 146 is connected to a fixed plate 148 via a spring 147, all of which are disposed in applicator tip 140 at a position proximal to the stack of patches 150. Fixed plate 148 may have an area equal to or smaller than a cross-section area of lumen 136 and may be fixed to a sidewall of lumen 136 via an adhesive, sonic welding, or the like. Plunger 146, spring 147, and fixed plate 148 may be any material known in the art, including but not limited to a medical grade metal alloy, a plastic, a resin, or a rubber, suitable for being used to place pressure against the stack of regenerative patches 150 and push the stack of patches 150 toward a distal opening of applicator tip 140.

With continued reference to FIG. 7A, the stack of patches 150 may include a first patch 151a having a first layer 152a including an adhesive substance and a second layer 154a, including a non-adhesive surface 154a1, so that adjacent patches 150 do not adhere to one another, and an adhesive surface 154a2, which may include the same material as first layer 152a. As described herein, first layer 152a may include a regenerative agent, an adhesive regenerative agent, or any other agent and/or attachment mechanism for attaching first patch 151a to target 160.

Prior to a first application, first patch 151a is partially exposed from applicator tip 140, outside of the distal opening of the applicator tip 140 such that non-adhesive surface 154a1 is adjacent to and/or contacts an outer surface of annular ring 144, thereby exposing first layer 152a outside applicator tip 140, as will be described in greater detail herein. Adhesive surface 154a2 is attached to a first layer 152b of a second patch 151b, as shown in FIG. 7A. Second patch 151b also includes a second layer 154b having a non-adhesive layer 154b1 and an adhesive surface 154b2. A patch 151n, which is a proximalmost patch, has an adhesive surface 154n1, which attaches to plunger 146 (n is a number of patches in the stack of patches 150, and may be a maximum number of patches in the stack of patches 150 that can be disposed in applicator tip 140). First layer 152a is applied to target 160, e.g., a tissue or another suitable target site, as will be described herein. It will be understood that target 160 may be any tissue known in the art, including but not limited to endomucosal tissue, gastrointestinal tissue, bone tissue, cartilage, etc.

An operation of endoscopic applicator 110 illustrated in FIGS. 7B and 7C will now be described. Endoscopic applicator 110 is introduced to the body in a same manner an endoscopic applicator 10 in FIGS. 1-3, as described above. After positioning applicator tip 140 at the desired location, e.g., at target 160, placement of one or more of the stack of patches 150 is performed. Handle 120 is maneuvered to push the distalmost portion of applicator tip 140 in FIG. 7B, including annular ring 144, in a direction indicated by arrow B and against target 160. Pushing applicator tip 140 against target 160 causes a surface of first layer 152a, opposite a surface of second layer 154a contacting annular ring 144, to contact and adhere to tissue 160. Subsequently, as shown in FIG. 7C, applicator tip 140 is pulled in a direction indicated by arrow D, via handle 120, which causes the remainder of patch 151a to exit applicator tip 140. If necessary to completely deploy all of patch 151a against target 160, handle 120 and applicator tip 140 are again moved in the direction indicated by arrow B in FIG. 7B, such that annular ring 144 presses against a surface 154b1 of second layer 154b of second patch 151b, as shown in FIG. 7B, causing first patch 151a to adhere to target 160. Applicator tip 140 is again moved in a direction indicated by arrow D in FIG. 7C, which pulls first layer 152b of second patch 151b from surface 154a2 of first patch 151a. Spring 148 forces plunger 146 against patch 151n, thereby forcing the stack of regenerative patches 150 toward the distal end of applicator tip 140, allowing second patch 151b to be applied to the same target 160 or a different target. As shown in FIG. 7C, second patch 151b is set to be applied to another location on target 160. As further shown in FIG. 7C, second layer 154a remains attached to first layer 152a, but the embodiment is not limited to this configuration, since second layer 154a may be released from first layer 152a during and/or subsequent to application of first patch 151a to target 160.

According to another embodiment, an applicator tip 240 is illustrated in FIG. 8A, and has similar features as applicator tip 40, described above. As shown in FIG. 8A, a stack of patches 250 is disposed in applicator tip 240 for application to a target 260, as explained herein. The stack of patches 250, including first patch 251a having a first layer 252a and a second layer 254a, and including second patch 251b having a first layer 252b and a second layer 254b, are applied to target 260 using a plunger 234 attached to a wire 232 in a manner as described above with reference to FIGS. 4A-5B. Applicator tip 240 according to an embodiment is used with, e.g., handle 20 shown in FIG. 2.

An operation of an endoscopic applicator, such as endoscopic applicator 10 in FIG. 1, having an applicator tip 240 will now be described. Applicator tip 240 is inserted into the body through the opening and advanced to the desired deployment site, e.g., the GI tract, as in the previous embodiments. After positioning applicator tip 240 at the desired location, deployment and placement of the stack of patches 250 is performed, in any manner described above.

As shown in FIG. 8A, first patch 251a adheres to target 260 via first layer 252a. As shown in FIG. 8B, after first patch 251a is attached to target 260, second layer 254a disengages or disconnects from, or otherwise falls off of, a back side (e.g., a side opposite target 260) and is passed from the body via normal excretion, is retrieved by another tool, and/or is biodegradable. After application of first patch 251a, applicator tip 240 is moved to another application location, e.g., a position adjacent first patch 251a, and the application of second patch 251b is performed. In this manner, one or more patches 251n from the stack of patches 250 is applied to the same target 260, or a different target. While handle 20, including spool 24, is described in the operation of applicator tip 240, the application device (e.g., spring 147, fixed plate 148, and plunger 146) illustrated in FIG. 7A may alternatively be used with applicator tip 240 to advance patches 250 along applicator tip 240 during application.

According to another embodiment, an applicator tip 340 is illustrated in FIG. 9. Like reference numerals will be used to describe like elements.

Applicator tip 340 is disposed at a distal end of a catheter (such as catheter 30 shown in FIG. 1). Applicator tip 340 includes an outer wall 342 and an annular ring 344, like those in prior embodiments.

The stack of patches 350 includes a plurality of patches as described herein. Each of the plurality of patches has a first layer, e.g., 352a, and a second layer, e.g., 354a. As shown in FIG. 9, each second layer, e.g., 354a, is attached to a pulley system 338, as will be described herein.

As shown in FIG. 9, a stack of patches 350 are disposed in applicator tip 340 for application to a target 360. One or more of patches 350 are applied to target 360 using a plunger 334 attached to a wire 332 disposed in a first lumen 336a in a manner as described above with reference to FIGS. 4A-5B. First lumen 336a and a second lumen 336b may include a pulley system, as shown in FIG. 9. The pulley system may include a wire or cable 338 that may extend around a pulley 339 at a distalmost end of applicator tip 340 and into a second lumen 336b, adjacent first lumen 336a, and which extends to a proximal end of a catheter, e.g., catheter 30 described herein. Cable 338 may attach to each of the second layers (e.g., second layer 354a) at connection points 370. Alternatively, applicator tip 340 may be formed without second lumen 336b, and cable 338 may extend on an outer side of applicator tip 340. As a further alternative, pulley 339 may be located within one or more lumens of the catheter so no parts of the pulley system are outside of the catheter. Cable 338 extends to a handle, e.g., handle 20, to allow a user to manipulate cable 338, as will be described herein. Applicator tip 340 according to an embodiment is used with handle 20 shown in FIG. 2.

An operation of an endoscopic applicator, such as endoscopic applicator 10 in FIG. 1, having an applicator tip 340 will now be described. Applicator tip 340 is inserted into the body through the opening and advanced to the desired deployment site, e.g., the GI tract, in any of the manners described above. After positioning applicator tip 340 at the desired location, deployment and placement of the stack of patches 350 is performed, in any manner described above. As shown in FIG. 9, first layer 352a was previously adhered to target 360. Subsequently, while continuing to push spool 24 toward distal end 20a of handle 20, an endoscopic applicator (including handle 20, catheter 30, and applicator tip 340) is pulled in a proximal direction, as indicated by arrow D in FIG. 5A. As shown in FIG. 9, first layer 352a adheres to target 360. After first layer 352a is attached to target 360, second layer 354a, which is attached to cable 338, is detached from first layer 352a and pulled proximally inside second lumen 336b. Cable 338 may be operated in any manner known in the art, for example by a user or by a motor (not shown). Alternatively, or additionally, cable 338 may pull second layer 354a on an external side of applicator tip 340.

After application of first layer 352a, applicator tip 340 is moved to another application location, e.g., a position adjacent first layer 352a, and the application of a first layer of second patch 351b is performed. In this manner, one or more patches from the stack of patches 350 is applied to target 360. While handle 20, including spool 24, is described in the operation of applicator tip 340, the application device (e.g., spring 147, fixed plate 148, and plunger 146) illustrated in FIG. 7A may alternatively be used with applicator tip 340 to advance patches 350 along applicator tip 340 during.

According to another embodiment, applicator tips 440 and 540 will be described with reference to FIGS. 10A-11B.

Figure 10A:
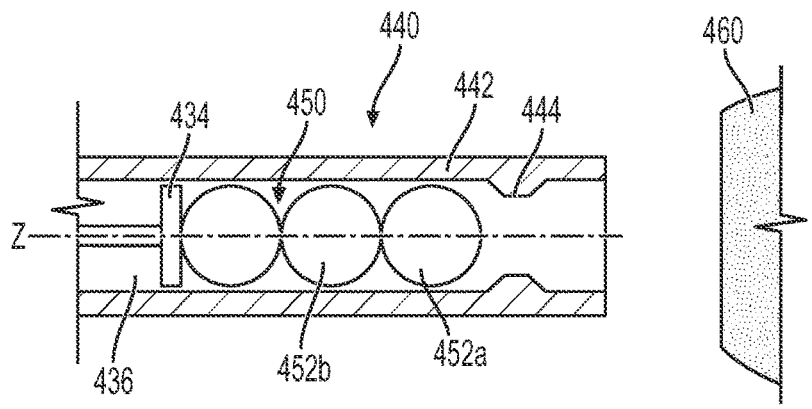
FIGS. 10A-10D are cross-sections of an applicator tip according to another embodiment.
Figure 10B:
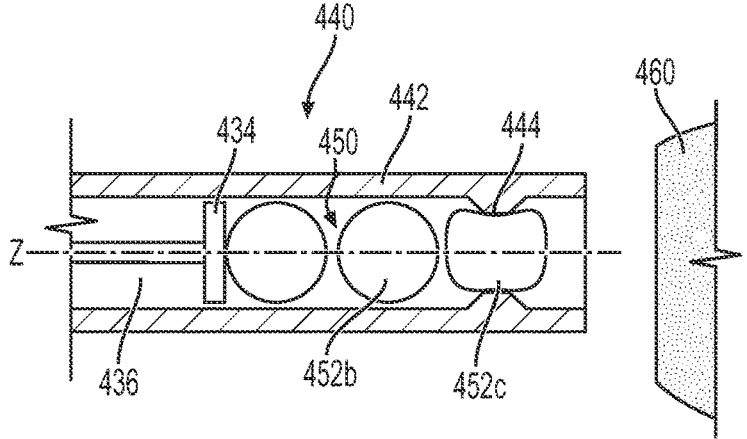

As shown in FIG. 10A, an applicator tip 440 is disposed at a distal end of a catheter (such as catheter 30 shown in FIG. 1). Applicator tip 440 includes an outer wall 442 having a generally circular cross-section. Applicator tip 440 is the distalmost portion of the catheter. Applicator tip 440 further includes a protrusion 444 extending into a lumen 436 of applicator tip 440. Protrusion 444 may be an annular protrusion, or one or more protrusions, that extends over less than a full circumference of lumen 436. A distance from central axis Z to an innermost portion of protrusion 444 is less than a distance from central axis Z to an innermost surface of outer wall 442. Protrusion 444 secures a plurality of spheres or balls 450 in applicator tip 440 until a force applied to the plurality of spheres 450, e.g., provided by a plunger 434, forces the distalmost ball past protrusion 444.

A stack of spheres 450 includes a plurality of spheres 452a, 452b, etc. as described herein. Each of the plurality of spheres, e.g., 452a, 452b, has a reagent, e.g., 454a (see FIG. 10D), provided within for application to a target 460. One or more of the stack of spheres 450 are applied to target 460 using a plunger 434 in a manner as described above with reference to FIGS. 4A-5B. Applicator tip 440 according to an embodiment is used with handle 20 shown in FIG. 2.

Figure 11A:
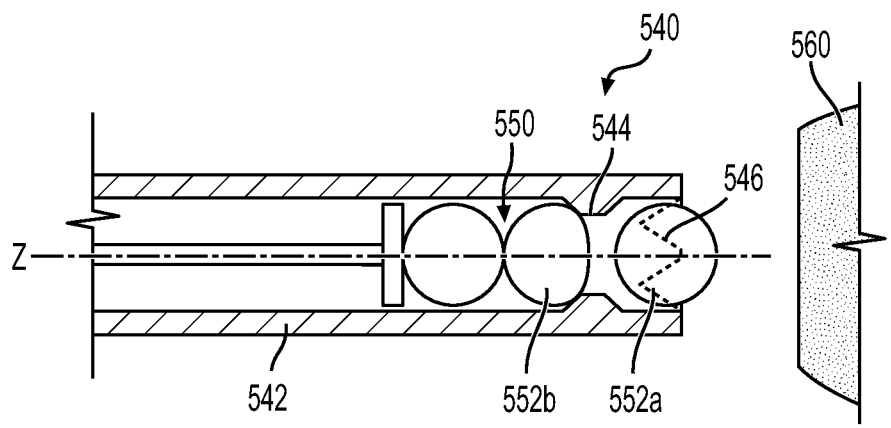
FIGS. 11A-11B are cross-sections of an applicator tip according to yet another embodiment.

With reference to FIG. 11A, an applicator tip 540, similar to applicator tip 440, will be described. Applicator tip 540 is disposed at a distal end of a catheter (such as catheter 30 shown in FIG. 1). Applicator tip 540 includes an outer wall 542 and a protrusion 544, like those in prior embodiments. Applicator tip further includes one or more blades 546 (or other cutting elements) distal of annular protrusion 544. Blades 546 are used to cut through an outer shell, which may be a rigid or deformable shell containing a substance container therein, of each of the plurality of spheres 550 during application to target 560, as described herein.

The plurality of spheres 550 include, e.g., spheres 552a, 552b, etc., and including a reagent, e.g., 554a, as described herein with reference to applicator tip 440.

An operation of applicator tip 440 and 540 will now be described with reference to FIGS. 10A-10D and 11A-11B. Applicator tips 440 or 540 are inserted into the body through the opening and advanced to the desired deployment site, e.g., the GI tract, in any of the manners described above. After positioning applicator tips 440 and 540 at the desired location, deployment and placement of the plurality of spheres 450 or 550 is performed in any manner described above.

Figure 10C:
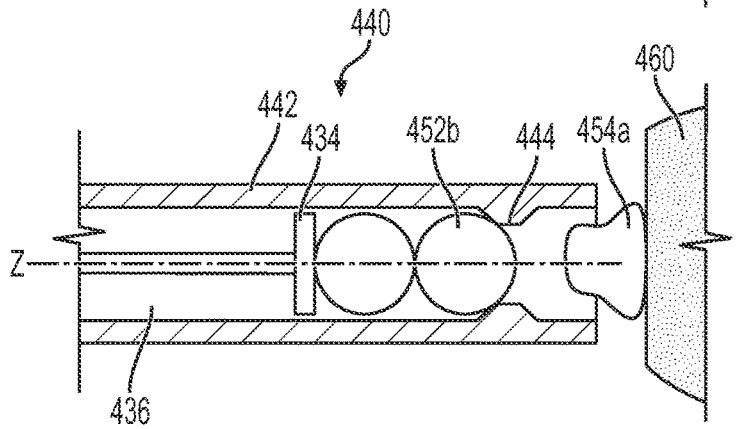
Figure 10D:
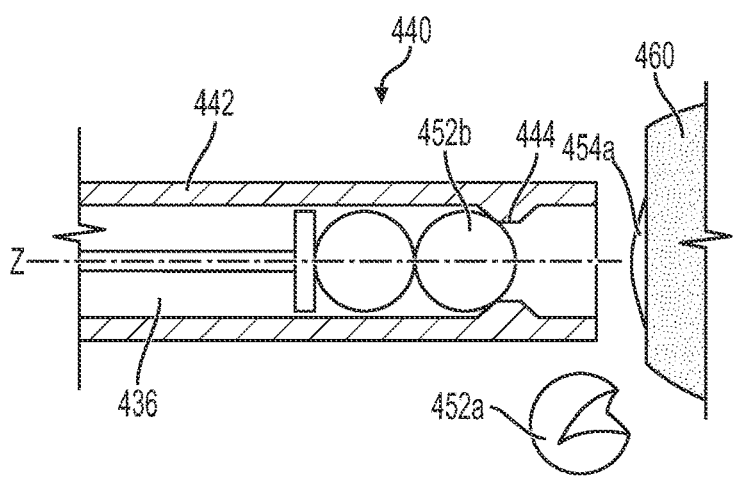

With reference to FIG. 10C, a first ball 452a is forced from applicator tip 440 and against target 460. The pressure between first sphere 452a and target 460 and/or applicator tip 440 causes first ball 452a to rupture, thereby releasing a first reagent 454a, which coats target 460. First reagent 454a may be hydrophilic and or otherwise designed to be attracted to target 460.

Figure 11B:
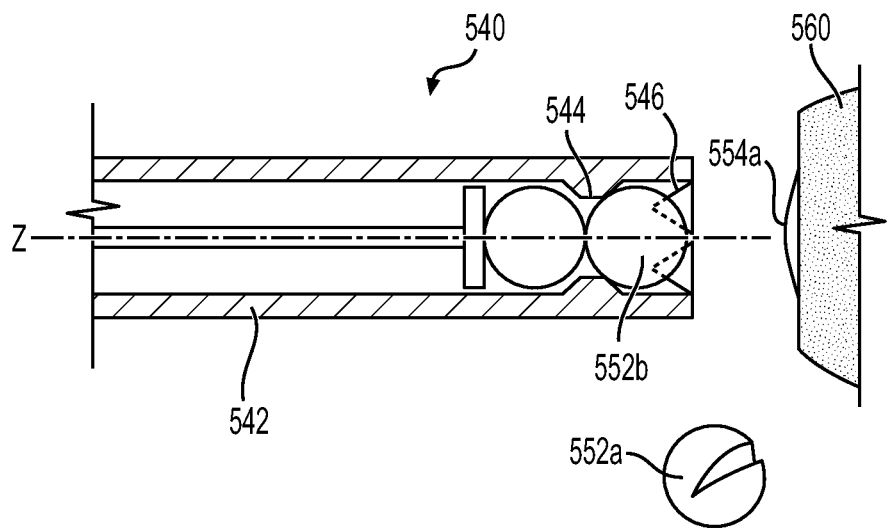

Dispensing the plurality of spheres 550 using applicator tip 540 may be performed, as shown in FIGS. 11A and 11B. A first sphere 552a is forced past annular protrusion 544 and out a distal end of applicator tip 540. As first ball 552a is dispensed, an outer layer of first ball 552a is cut by one or more blades 546, thereby releasing a first reagent 554a, which coats target 560. After application of first reagents 454a, 554a, applicator tips 440 or 540 are moved to another application location, e.g., a position adjacent the application area or another target area, and the application of another reagent using second spheres 452b, 552b is performed. In this manner, reagents from one or more spheres from the stack of spheres 450, 550 are applied to targets 460, 560, respectively.

According to another embodiment, an applicator tip 640 is illustrated in FIGS. 12A and 12B. Like reference numerals will be used to describe like elements.

Applicator tip 640 is disposed at a distal end of a catheter (such as catheter 30 shown in FIG. 1). Applicator tip 640 includes an outer wall 642 having a generally circular cross-section and an annular ring 644, similar to applicator tip 40.

The stack of patches 650 includes a plurality of patches 651a, 651b, etc. as described herein. Each of the plurality of patches has a first layer, e.g., 652a, and a spacer, e.g., 654a. As shown in FIG. 12B, each spacer, e.g., 654a, separates from each first layer e.g., 652a, after application to target 660, as will be described herein.

As shown in FIG. 12A, a stack of patches 650 are disposed in applicator tip 640 for application to a target 660, as explained herein. The stack of patches 650 are applied to target 660 in any manner described above. For example, applicator tip 640 according to an embodiment is used with handle 20 shown in FIG. 2.

An application of the stack of patches 650 will be described with reference to FIGS. 12A and 12B. Applicator tip 640 is inserted into the body through the opening and advanced to the desired deployment site, e.g., the GI tract, in any manner described herein. After positioning applicator tip 640 at the desired location, deployment and placement of the stack of patches 650 is performed, similar to the manner described with respect to the embodiments above. After patch 651a is attached to target 660, first separator 654a is detached from first layer 652a. Separator 654a may be biodegradable. Alternatively, or additionally, separator 654a may be small enough to pass through the body and be excreted during normal bowel movements by a patient, or may be removed by a tool.

After application of first patch 651*a*, applicator tip 640 is moved to another application location, e.g., a position adjacent first patch 651*a* or another target site, and the application of second patch 651*b* is performed. In this manner, one or more patches from the stack of regenerative 650 is applied to target 660.

It will be understood that, unless specifically set forth herein, any material known in the art may be used for the various elements. For example, features may include a medical grade plastic or rubber, a ceramic, a metal, or a combination thereof. Spacers and/or separation layers may be may include a material that is biodegradable and/or may include one or more of a medical grade plastic or rubber, a ceramic, a metal, or a combination thereof, such as polyvinyl acetate (PVA), polyhydroxyethylmethacrylate (PHEMA), polytetrafluoroethylene (PTFE), HDPE (high-density polyethylene), polydimethylsiloxane (PDMS), polyurethane (PU), and/or poly(methyl methacrylate) (PMMA). The attachment agent(s) may be one or more biocompatible materials and may be adhesive prior to introduction into a body lumen and/or may be activated by moisture. Further, the regenerative agent may include an adhesive agent as described above, and/or may be any agent now known or later developed for the treatment of the inner walls of a human body, such as the GI tract.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A medical dispensing device, comprising:
a catheter defining a lumen having a longitudinal axis and a distal opening;
an actuator disposed in the lumen and movable along the longitudinal axis;
a plurality of reagent containers disposed in the lumen proximal to the distal opening and distal to the actuator, the plurality of reagent containers being stacked along the longitudinal axis for dispersement, one reagent container at a time, through the distal opening via a force applied by the actuator; and
one or more blades disposed at the distal opening and configured to cut each reagent container of the plurality of reagent containers, wherein each reagent container of the plurality of reagent containers is deformable.

2. The medical dispensing device of claim 1, wherein the actuator is a plunger.

3. The medical dispensing device of claim 1, wherein each reagent container of the plurality of reagent containers has a spherical shape.

4. The medical dispensing device of claim 1, wherein each reagent container of the plurality of reagent containers is rigid.

5. The medical dispensing device of claim 1, wherein a first reagent container of the plurality of reagent containers includes a first reagent, and wherein a second reagent container of the plurality of reagent containers includes a second reagent.

6. The medical dispensing device of claim 5, wherein the first reagent container is adjacent to the second reagent container.

7. The medical dispensing device of claim 1, wherein the one or more blades are configured to expose a reagent within each reagent container of the plurality of reagent containers.

8. The medical dispensing device of claim 1, wherein a protrusion extends from a sidewall defining the lumen, toward the longitudinal axis, and distal to a distalmost reagent container of the plurality of reagent containers.

9. The medical dispensing device of claim 8, wherein the one or more blades are disposed distal to the protrusion.

10. The medical dispensing device of claim 8, wherein the protrusion is annular.

11. The medical dispensing device of claim 8, wherein the one or more blades extend from the sidewall defining the lumen.

12. A medical dispensing device, comprising:
a catheter defining a lumen having a distal opening;
an actuator disposed in the lumen and movable within the lumen;
a plurality of reagent containers disposed in the lumen between the distal opening and the actuator, wherein a force applied by the actuator delivers one reagent container at a time, through the distal opening;
one or more blades disposed at the distal opening and configured to cut each reagent container of the plurality of reagent containers to release a reagent contained within each reagent container of the plurality of reagent containers; and
a protrusion extending inward from a sidewall defining the lumen and distal to the plurality of reagent containers, wherein the one or more blades extend inward from the sidewall defining the lumen and distal to the protrusion.

13. The medical dispensing device of claim 12, wherein the actuator is a plunger.

14. The medical dispensing device of claim 12, wherein each reagent container of the plurality of reagent containers is a sphere.

15. The medical dispensing device of claim 12, wherein a first subset of the plurality of reagent containers includes a first reagent, and wherein a second subset of the plurality of reagent containers includes a second reagent.

16. The medical dispensing device of claim 12, wherein a protrusion extends inward from a sidewall defining the lumen and distal to the plurality of reagent containers.

17. The medical dispensing device of claim 16, wherein the protrusion is configured to maintain a position of the plurality of reagent containers within the lumen.

18. A medical dispensing device, comprising:
a catheter defining a lumen having a longitudinal axis and a distal opening;
an actuator disposed in the lumen and movable along the longitudinal axis;
a plurality of reagent containers disposed in the lumen proximal to the distal opening and distal to the actuator, the plurality of reagent containers being stacked along the longitudinal axis for dispersement, one reagent container at a time, through the distal opening via a force applied by the actuator;
one or more blades disposed at the distal opening and configured to cut each reagent container of the plurality of reagent containers; and a protrusion extending from a sidewall defining the lumen, toward the longitudinal axis, and distal to a distalmost reagent container of the plurality of reagent containers, wherein the one or more blades are disposed distal to the protrusion.

* * * * *